(12) United States Patent
Takeuchi et al.

(10) Patent No.: US 9,315,828 B2
(45) Date of Patent: *Apr. 19, 2016

(54) PROMPT NUCLEIC ACID DELIVERY CARRIER COMPOSITION

(75) Inventors: Hirofumi Takeuchi, Gifu (JP); Yasuyuki Hira, Gifu (JP); Koji Nakano, Gifu (JP); Hidekazu Toyobuku, Tokushima (JP)

(73) Assignees: Hirofumi Takeuchi, Gifu (JP); OTSUKA PHARMACEUTICAL CO., LTD., Tokyo (JP)

( * ) Notice: Subject to any disclaimer, the term of this patent is extended or adjusted under 35 U.S.C. 154(b) by 0 days.

This patent is subject to a terminal disclaimer.

(21) Appl. No.: 12/532,949

(22) PCT Filed: Mar. 26, 2008

(86) PCT No.: PCT/JP2008/055730
§ 371 (c)(1),
(2), (4) Date: Sep. 24, 2009

(87) PCT Pub. No.: WO2008/117828
PCT Pub. Date: Oct. 2, 2008

(65) Prior Publication Data
US 2010/0063131 A1 Mar. 11, 2010

(30) Foreign Application Priority Data
Mar. 26, 2007 (JP) .................................. 2007-79944

(51) Int. Cl.
*A61K 48/00* (2006.01)
*C07H 21/02* (2006.01)
*C12N 15/88* (2006.01)
*C12N 15/87* (2006.01)
*A61K 9/127* (2006.01)
*A61K 31/7088* (2006.01)
*A61K 31/713* (2006.01)
*C12N 15/11* (2006.01)

(52) U.S. Cl.
CPC ............... *C12N 15/87* (2013.01); *A61K 9/127* (2013.01); *A61K 31/7088* (2013.01); *A61K 31/713* (2013.01); *C12N 15/111* (2013.01); *A61K 48/00* (2013.01); *C12N 2310/14* (2013.01); *C12N 2320/32* (2013.01)

(58) Field of Classification Search
None
See application file for complete search history.

(56) References Cited

U.S. PATENT DOCUMENTS

| | | | |
|---|---|---|---|
| 5,776,488 A | 7/1998 | Mori et al. | |
| 6,126,964 A | 10/2000 | Wolff et al. | |
| 6,740,335 B1 | 5/2004 | Moynihan et al. | |
| 6,835,395 B1 | 12/2004 | Semple et al. | |
| 7,119,078 B2* | 10/2006 | Jing et al. | 514/44 R |
| 7,166,745 B1 | 1/2007 | Chu et al. | |
| 2002/0102297 A1* | 8/2002 | Safinya et al. | 424/450 |
| 2004/0208921 A1* | 10/2004 | Ho et al. | 424/450 |
| 2005/0064024 A1* | 3/2005 | Vadrucci et al. | 424/450 |
| 2005/0064595 A1* | 3/2005 | MacLachlan et al. | 435/458 |
| 2005/0142114 A1* | 6/2005 | Gieseler et al. | 424/93.2 |
| 2005/0238706 A1 | 10/2005 | Ahmad et al. | |
| 2006/0025366 A1 | 2/2006 | MacLachlan et al. | |
| 2006/0030578 A1 | 2/2006 | Ahmad et al. | |
| 2006/0134189 A1 | 6/2006 | MacLachlan et al. | |
| 2011/0009641 A1* | 1/2011 | Anderson et al. | 548/340.1 |

FOREIGN PATENT DOCUMENTS

| | | |
|---|---|---|
| EP | 1759691 A1 | 3/2007 |
| JP | 10-313872 A | 12/1998 |
| JP | 11-292795 A | 10/1999 |
| JP | 2002-529439 A | 9/2000 |
| JP | 2005-508394 A | 3/2005 |
| JP | 2005-336081 A | 12/2005 |
| WO | 95/24201 A1 | 9/1995 |
| WO | 99/13816 A2 | 3/1999 |
| WO | 2004/017940 A2 | 3/2004 |
| WO | 2005/007196 A2 | 1/2005 |
| WO | 2005/102268 A2 | 11/2005 |
| WO | 2006/002538 A1 | 1/2006 |
| WO | WO 2007/048019 * | 4/2007 |
| WO | 2009/061003 A2 | 5/2009 |

OTHER PUBLICATIONS

Takano et al (Pharmaceutical Research, vol. 20, No. 7, Jul. 2003).*
Product information for L-alpha-phosphatidylcholine from Sigma Chemical Company, retrieved from http://www.sigmaaldrich.com/catalog/product/sigma/61755?lang=en&region=US on Oct. 15, 2013.*
International Search Report mailed May 27, 2008 in PCT/JP2008/055730.

(Continued)

*Primary Examiner* — Richard Schnizer
(74) *Attorney, Agent, or Firm* — Sughrue Mion, PLLC

(57) ABSTRACT

An object of the present invention is to provide a carrier composition for nucleic acid delivery, which can efficiently deliver a nucleic acid into cells when a nucleic acid such as siRNA is administered to animal-derived cells or animals, and also has low toxicity and high safety, and a composition for nucleic acid delivery containing the carrier composition and nucleic acid.

A carrier for nucleic acid delivery is prepared by using (A) a diacylphosphatidylcholine, (B) at least one member selected from the group consisting of cholesterol and derivatives thereof, and (C) an aliphatic primary amine. Also, a composition for nucleic acid delivery is prepared by mixing the carrier for nucleic acid delivery with a nucleic acid.

7 Claims, 2 Drawing Sheets

(56) References Cited

OTHER PUBLICATIONS

Extended European Search Report issued in corresponding EP Application No. 08738918.5 on Aug. 9, 2011 (in the name of Otsuka Pharmaceutical Co., Ltd. et al.).
Maria Kokkona et al., "Stability of SUV liposomes in the presence of cholate salts and pancreatic. ipases: effect of lipid composition", European Journal of Pharmaceutical Sciences, 2000, 9: 245-252.

Yoshie Maitani et al., "Physicochemical Characteristics and Transfection Efficienty of DNA in Liposomes with Soybean-Derived Sterylglucoside into HepG2 Cells", J. Pharm. Sci. Technol., Japan, 2001, 61(1): 1-10.
Office Action issued Apr. 8, 2013, in corresponding European Patent Application No. 08738918.5.

* cited by examiner

Concentration of constituent lipid in carrier for nucleic acid delivery (in terms of DSPC concentration) (mg/mL)

PROMPT NUCLEIC ACID DELIVERY CARRIER COMPOSITION

TECHNICAL FIELD

The present invention relates to a carrier composition for nucleic acid delivery which can efficiently deliver a nucleic acid into cells when a nucleic acid is administrated to animal-derived cells or organisms, and which also has low toxicity and high safety; and to a composition for nucleic acid delivery.

BACKGROUND ART

Various types of nucleic acids which exert physiologically active functions within cells have been discovered through recent developments in biotechnology. For example, it is known that small interfering RNA (siRNA) induces degradation of mRNA of a target gene existing within cells and inhibits expression of the target gene (RNA interference). The inhibitory function against target gene expression due to the RNA interference is useful for mitigation or treatment of disease symptoms caused by irregular expression of particular genes or gene groups, and development of therapeutic agents using siRNA is expected. To utilize nucleic acids including siRNA as therapeutic agents, it is important that siRNA functions in the target cell, and therefore, it is essential to establish efficient techniques to deliver the nucleic acids into target cells.

Use of a carrier (vector) is known as a technique to deliver exogenous nucleic acid molecules or genes into cells. Vectors include virus vectors and nonvirus vectors. Virus vectors have high gene transfer efficiency; however, there are various unknown safety aspects including pathogenicity, immunogenicity and cytotoxicity. Therefore, development of safer nonvirus vectors is awaited.

As a nonvirus nucleic acid delivery carrier that promotes delivery of a nucleic acid, such as siRNA, into cells, for example, a cationic lipid with a specific structure has been reported in Patent Document 1. However, the cationic lipid reported in Patent Document 1 has a disadvantage that it shows toxicity when administered to cultured cells or living organisms. Also, Patent Document 2 discloses a composition containing an amphiphilic compound and a polycation as a carrier composition which has comparatively low toxicity and can deliver siRNA into cells. However, the composition reported in Patent Document 2 also has a safety problem since its cytotoxicity becomes non-negligible when a sufficient amount of siRNA is introduced into cells.

In light of the prior art, development of a carrier composition for nucleic acid delivery which has low toxicity and can efficiently deliver a nucleic acid, such as siRNA, into cells has been desired.

[Patent Document 1] Japanese Unexamined Patent Publication No. 2002-529439
[Patent Document 2] Japanese Unexamined Patent Publication No. 2005-508394

DISCLOSURE OF THE INVENTION

Technical Problem

Thus, an object of the present invention is to solve the above problems of the prior art. Specifically, an object of the present invention is to provide a carrier composition for nucleic acid delivery, which can efficiently deliver nucleic acid into cells when a nucleic acid such as siRNA is administered to animal-derived cells or animals, and also has low toxicity and high safety; and a composition for nucleic acid delivery containing the carrier composition and nucleic acid. Also, an another object of the present invention is to provide a method for introducing a nucleic acid into cells, which can efficiently deliver the nucleic acid into cells with high safety.

Means for Solving the Problem

The present inventors have intensively studied so as to achieve the above object and found that a composition containing (A) a diacylphosphatidylcholine, (B) cholesterol and/or a derivative thereof and (C) an aliphatic primary amine has low toxicity and high safety, can efficiently deliver a nucleic acid into cells, and is therefore useful as a carrier for nucleic acid delivery. They have also found that it is possible to impart more excellent safety and nucleic acid-introducing properties by using a composition containing the components (A) to (C) after forming into a liposomal form. The present invention has been completed by making further improvement based on these findings.

Namely, the present invention provides the following embodiments.

Item 1. A carrier composition for nucleic acid delivery, comprising (A) a diacylphosphatidylcholine, (B) at least one member selected from the group consisting of cholesterol and derivatives thereof, and (C) an aliphatic primary amine.

Item 2. The carrier composition for nucleic acid delivery according to Item 1, wherein the component (A) is a diacylphosphatidylcholine whose acyl group moiety has 4 to 23 carbon atoms.

Item 3. The carrier composition for nucleic acid delivery according to Item 1 or 2, wherein the component (B) is cholesterol.

Item 4. The carrier composition for nucleic acid delivery according to Item 1, wherein the component (C) is an alkylamine having 10 to 20 carbon atoms.

Item 5. The carrier composition for nucleic acid delivery according to Item 1,
wherein the component (A) is at least one member selecting from the group consisting of dimyristoylphosphatidylcholine, dipalmitoylphosphatidylcholine, and distearoylphosphatidylcholine;
the component (B) is cholesterol; and
the component (C) is stearylamine.

Item 6. The carrier composition for nucleic acid delivery according to Item 1, wherein the molar ratio of component (A):component (B):component (C) is 5-9:1-5:1.

Item 7. The carrier composition for nucleic acid delivery according to Item 1, which is a carrier for delivery of siRNA.

Item 8. The carrier composition for nucleic acid delivery according to Item 1, which is a liposome preparation in which a liposomal membrane is formed of the components (A) to (C).

Item 9. A composition for nucleic acid delivery, comprising a nucleic acid, and the carrier composition for nucleic acid delivery of Item 1.

Item 10. The composition for nucleic acid delivery according to Item 9, wherein the nucleic acid is siRNA.

Item 11. The composition for nucleic acid delivery according to Item 9, which is a liposome preparation.

Item 12. A method for introducing a nucleic acid, which comprises the step of introducing the nucleic acid into cells by bringing the composition for nucleic acid delivery of Item 9 into contact with the cells.

Item 13. A method for introducing a nucleic acid according to Item 12, wherein the cells are cultured cells, cells separated from living organisms, or cells existing in living organisms.

Item 14. Use of a composition comprising (A) a diacylphosphatidylcholine, (B) at least one member selected from the group consisting of cholesterol and derivatives thereof, and (C) an aliphatic primary amine, in the manufacture of a carrier for nucleic acid delivery.

Item 15. Use according to Item 14, wherein the carrier is used for delivery of siRNA.

EFFECTS OF THE INVENTION

The carrier composition for nucleic acid delivery and the composition for nucleic acid delivery of the invention have an advantage that they can effectively deliver a nucleic acid into cells thereby exerting a useful function of the nucleic acid in cells, and also has low toxicity and high safety. Therefore, the carrier composition for nucleic acid delivery and the composition for nucleic acid delivery are useful for treatment of various diseases by introduction of a nucleic acid, particularly treatment of intractable diseases which are difficult to be treated by a low molecular compound.

The carrier composition for nucleic acid delivery and the composition for nucleic acid delivery of the invention are particularly preferred to introduce siRNA into cells since induction of interferon expression, which is an adverse reaction of siRNA, can be effectively suppressed.

Furthermore, the composition for nucleic acid delivery of the invention also has an advantage that the composition can be stored in a freeze-dried state since it can be subjected to a freeze-drying treatment.

BEST MODE FOR CARRYING OUT THE INVENTION

Figure 1:
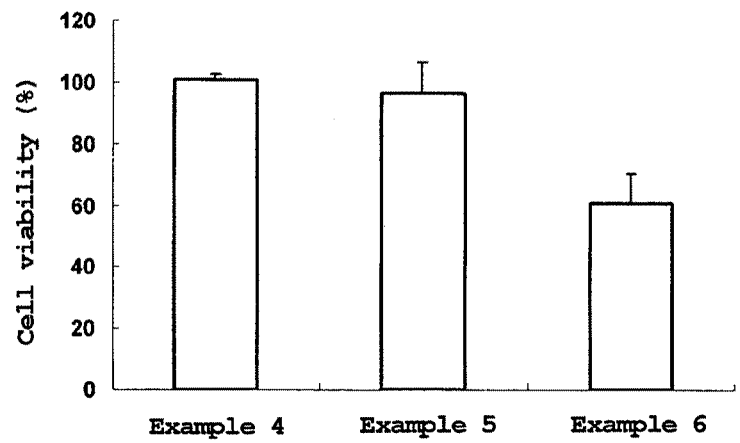
FIG. 1 shows the results of Test Example 1, i.e., the results of the evaluation of a composition for nucleic acid delivery on safety for cells.

The present invention will now be described in detail.
Carrier for Nucleic Acid Delivery The carrier composition for nucleic acid delivery of the invention comprises (A) a diacylphosphatidylcholine, (B) cholesterol and/or a derivative thereof, and (C) an aliphatic primary amine.

The carrier composition for nucleic acid delivery of the invention is used as a nucleic acid carrier for delivery (introduction) of a nucleic acid into cells.

The type and structure of the nucleic acid to which the carrier composition for nucleic acid delivery of the present invention is applied is not limited as long as it is required to be delivered into cells. Specific examples of such nucleic acids include siRNA, mRNA, tRNA, rRNA, cDNA, miRNA (microRNA), ribozyme, antisense oligodeoxynucleotide, decoy oligonucleotide, plasmid DNA, peptide nucleic acid, triplex forming oligonucleotide (TFO), aptamer, and genes. Particularly, the carrier composition for nucleic acid delivery of the invention has the useful feature of inhibiting induction of interferon expression, which is an adverse reaction of siRNA, and thus it is useful to deliver siRNA into cells. Nucleic acids to which the carrier composition for nucleic acid delivery of the invention is applied may be derived from humans, animals, plants, bacteria and viruses, and also, it may be produced by chemical synthesis. In addition, these nucleic acids can be single, double or triple strand, and the molecular weight thereof is not specifically limited. Also, nucleic acids can be modified with chemical compounds, enzymes or peptides. In the invention, these nucleic acids may be used alone, or two or more kinds of them may be used in combination.

Diacylphosphatidylcholine (hereinafter, referred sometimes to as "component (A)") used in the carrier composition for nucleic acid delivery of the invention is not specifically limited as long as it is pharmacologically acceptable, and examples thereof include a diacylphosphatidylcholine whose acyl group moiety has 4 to 23 carbon atoms. The number of carbon atoms of two acyl groups constituting the diacylphosphatidylcholine may be the same or different.

Specific examples of the diacylphosphatidylcholine used in the present invention include dilauroylphosphatidylcholine, dimyristoylphosphatidylcholine, dipalmitoylphosphatidylcholine, distearoylphosphatidylcholine, dioleoylphosphatidylcholine, dilinoleoylphosphatidylcholine, myristoylpalmitoylphosphatidylcholine, myristoylstearoylphosphatidylcholine, palmitoylstearoylphosphatidylcholine, dibutyloylphosphatidylcholine, dihexanoylphosphatidylcholine, diheptanoylphosphatidylcholine, didecanoylphosphatidylcholine, diphthanoylphosphatidylcholine, didodecylphosphatidylcholine, dieicosenoylphosphatidylcholine, dihenicosanoylphosphatidylcholine, dierucoylphosphatidylcholine, diarachidonoylphosphatidylcholine, and bis(tricosadinoyl) phosphatidylcholine. Of these diacylphosphatidylcholines, a diacylphosphatidylcholine whose acyl group moiety has 12 to 18 carbon atoms is preferable; a diacylphosphatidylcholine whose acyl group moiety has 13 to 17 carbon atoms, such as dimyristoylphosphatidylcholine, dipalmitoylphosphatidylcholine, distearoylphosphatidylcholine, myristoylpalmitoylphosphatidylcholine, myristoylstearoylphosphatidylcholine, and palmitoylstearoylphosphatidylcholine is more preferable; dimyristoylphosphatidylcholine, dipalmitoylphosphatidylcholine, and distearoylphosphatidylcholine are particularly preferable; and distearoylphosphatidylcholine is most preferable. These diacylphosphatidylcholines may be used alone, or two or more kinds of them may be used in combination.

Cholesterol and/or a derivative thereof (hereinafter referred sometimes to as "component (B)") used in the carrier composition for nucleic acid delivery of the present invention is not specifically limited as long as it is pharmacologically acceptable. The derivative of cholesterol is a cationic lipid having a cholesterol skeleton, and specific examples thereof include 3β-[N—(N',N'-dimethylaminoethane)-carbamoyl] cholesterol (DC-Chol), 3β-[N',N',N'-trimethylaminoethane] cholesterol iodide (TC-Chol), bis(guanidium)-tren-cholesterose (BGTC), N-cholesteryloxycarbonyl-3,7-diazanonan-1,9-diamine, β-alanine-diethanolamine-cholesterol, $N^4$-spermine cholesteryl carbamate (GL-67), N[$N^4$-3-aminopropylspermidine]cholesteryl carbamate (GL-78), $N^4$-spermine cholesteryl carboxamide (GL-90), $N^1,N^8$-bis (arginine carboxamide)-N⁴-spermidine cholesteryl carbamate, and N-[N¹,N⁴,N⁸-tris(3-aminopropyl)spermidine]cholesteryl carbamate (GL-96). In the invention, the component (B) is preferably cholesterol. In the invention, as the component (B), cholesterol and derivative thereofs may be used alone, or two or more kinds of them may be used in combination.

The aliphatic primary amine (hereinafter referred sometimes to as "component (C)") used in the carrier composition for nucleic acid delivery of the invention is not specifically limited as long as it is pharmacologically acceptable, and examples thereof include an alkylamine whose alkyl group moiety has 10 to 20 carbon atoms.

Specific examples of the aliphatic primary amine used in the present invention include laurylamine, myristylamine, palmitylamine, stearylamine, oleylamine, decanoylamine, and phthanoylamine. Of these aliphatic primary amines, an alkylamine whose alkyl group moiety has 12 to 18 carbon atoms is preferable; stearylamine, oleylamine and palmitoylamine are more preferable; and stearylamine is particularly preferable. These dialiphatic primary amines may be used alone, or two or more kinds of them may be used in combination.

The carrier composition for nucleic acid delivery of the present invention may contain a combination of the components (A) to (C). In view of further enhancing efficiency of delivery of nucleic acid into cells and low toxicity by employing the following combinations, a combination of (A) a diacylphosphatidylcholine whose acyl group moiety have 4 to 23 carbon atoms, (B) cholesterol and/or a derivative thereof, and (C) an alkylamine having 10 to 20 carbon atoms is preferable and a combination of (A) dimyristoylphosphatidylcholine, dipalmitoylphosphatidylcholine and/or distearoylphosphatidylcholine, (B) cholesterol, and (C) stearylamine is more preferable.

In the carrier composition for nucleic acid delivery of the present invention, the ratio of the components (A) to (C) is not specifically limited. For example, the molar ratio component (A):component (B):component (C) is 5-9:1-5:1, preferably 6-9:1-4:1, and more preferably 7-8:2-3:1. Efficiency of delivery of a nucleic acid into cells and low toxicity can be further enhanced by satisfying the molar ratio.

The total amount of the components (A) to (C) based on the total amount of the carrier composition for nucleic acid delivery of the present invention is, for example, from 1 to 100% by weight, preferably from 20 to 90% by weight, and more preferably from 30 to 70% by weight.

The carrier composition for nucleic acid delivery of the present invention may contain, in addition to the components (A) to (C), other cationic lipids. Specific examples of the cationic lipid include cationic lipids bonded with a steroid, such as squalamine, 3a,7a,12a-tris(3-aminopropoxy)-5β-cholan-24-(N,N-bis(3-aminopropyl)amine, 3a,7a,12a-tris(3-aminopropoxy)-5β-cholan-24-(N—(N-(3-aminopropyl))-3-aminopropyl)-amine), 3a,7a,12a-tris(3-azidopropoxy)-5β-cholan-24-(N,N-bis(2-cyanoethyl)amine), and 3a,7a,12a-tris(3-azidopropoxy)-5β-cholan-24-(N-(benzyloxycarbonyl)N-(3-hydroxypropyl)-amine)); cationic lipids bonded with cholic acid, such as umbrella-spermine conjugates; cationic lipids bonded with sterolglycoside; cationic lipids bonded with steroidsaponin; and quaternary ammonium salt-type cationic lipids such as dimethyldioctadecylammonium bromide (DDAB), 1,2-dimyristoyl-3-trimethylammoniumpropane, 1,2-dioleoyl-3-trimethylammoniumpropane (DOTAP), 1,2-dioleoyl-3-trimethylammoniumpropanemethyl sulfate, 1,2-dipalmitoyl-3-trimethylammoniumpropane, 1,2-distearoyl-3-trimethylammoniumpropane, N-(1-(2,3-bis(oleoyloxy)propyl)-N,N,N-trimethylammonium hydrochloride (DOTMA), dimyristoyloxypropyldimethylhydroxyethylammonium bromide (DMRIE), dioleoyloxypropyldimethylhydroxyethylammonium bromide (DORIE), dimethyldidodecylammonium bromide, N-(a-trimethylammonioacetyl)-didodecyl-D-glutamine hydrochloride, N-(a-trimethylammonioacetyl)-O,O'-bis-(1H,1H,2H,2H-perfluorodecyl-L-glutamine hydrochloride, O,O'-didodecanoyl-N-(a-trimethylammonioacetyl)diethanolamine hydrochloride, methylallyldidodecylammonium bromide, N-{p-(w-trimethylammoniobutyloxy)-benzoyl}-didodecyl-L-glutamine hydrochloride, 9-(w-trimethylammoniobutyl)-3,6-bis(dodecanoyl)carbazole bromide, dimethyldioctadecylammonium hydrochloride, N-w-trimethylammoniodecanoyl-dihexadecyl-D-glutamine bromide, N-{p-(w-trimethylammoniohexyloxy)-benzoyl}-ditetradecyl-L-glutamine bromide, p-(w-trimethylammoniodecyloxy)-p'-octyloxyazobenzene bromide (MC-1-0810), p-{w-(b-hydroxyethyl)dimethyl-ammonio-decyloxy}-p'-octyloxyazobenzene bromide (MC-3-0810) , O,O',O"-tridodecanoyl-N-(w-trimethyl-ammoniodecanoyl)-tris(hydroxymethyl)aminomethane bromide (TC-1-12) , 1,2-dilaurylglycero-3-ethylphosphocholine, 1,2-dimyristoyl-glycero-3-ethylphosphocholine, 1,2-dipalmitoyl-glycero-3-ethylphosphocholine, 1,2-distearoyl-glycero-3-ethylphosphocholine, 1,2-dioleoyl-glycero-3-ethylphosphocholine, and 1-palmitoyl-2-oleoyl-glycero-3-ethylphosphocholine.

In the invention, when cationic lipids other than the components (A) to (C) are contained, the proportion of the cationic lipid is not specifically limited as long as the effects of the invention are not adversely affected. The proportion of the cationic lipid is from 1 to 10 parts by weight, preferably from 2 to 8 parts by weight, and more preferably from 4 to 6 parts by weight, per 100 parts by weight of the total amount of the components (A) to (C).

Furthermore, the carrier composition for nucleic acid delivery of the invention may contain an oily base, if necessary. By including an oily base and using its characteristics, it becomes possible to control the efficiency of the nucleic acid to be introduced by the carrier composition for delivery. For example, adjustment of the specific gravity of the carrier composition for nucleic acid delivery by including the oily base controls contact between the nucleic acid and the carrier composition for nucleic acid delivery and allows improvement of introduction efficiency in vitro. In addition, for example, by including a compound with a temperature-sensitive function as the oily base, fluctuation on a cell surface can be induced due to core disruption of a nucleic acid carrier composition under a given temperature condition, thereby improvement of introduction efficiency of nucleic acid become possible. Furthermore, for example, by including a compound with an external stimulation disruption property as the oily base, fluctuation on the cell surface can be induced due to core disruption of a nucleic acid carrier composition caused by external stimulation, thereby improvement of introduction efficiency of the nucleic acid become possible.

Examples of the oily base included in the carrier composition for nucleic acid delivery of the present invention include perfluorocarbon, perfluoropentane, perfluorooctyl bromide, perfluorohexane, perfluorotributylamine, soybean oil, refined soybean oil, hardened soybean oil, unsaponified soybean oil, squalene, castor oil, clove oil, sorbitan trioleate, turpentine oil, safflower oil, safflower oil fatty acid, oleic acid, coconut oil, rapeseed oil, fusel oil, olive oil, linseed oil, sesame oil, chlorophyll oil, croton oil, bergamot oil, cedar oil, orange oil, fennel oil, eucalyptus oil, corn oil, lavender oil, sweet majoram oil, lemon oil, cotton seed oil, egg york oil, rose oil, pine oil, almond oil, peanut oil, camellia oil, white camphor oil, chamomile oil, cinnamon oil, peppermint oil, esterified corn oil, bread oil, *Anthemis nobilis* oil, snake oil, spearmint oil, sunflower oil, cacao butter, wheat germ oil, zinc oxide oil, hardened oil, hydrogenated vegetable oil, light liquid paraffin, liquid paraffin, medium chain fatty acid triglyceride, mink oil, orange peel oil, polyoxyethylene castor oil, polyoxyethylene hardened castor oil, polyoxyethylene hardened castor oil 10, polyoxyethylene hardened castor oil 100, polyoxyethylene hardened castor oil 20, polyoxyethylene hardened castor oil 40, polyoxyethylene hardened castor oil 5, polyoxyethylene hardened castor oil 50, polyoxyethylene hardened castor oil 60, polyoxyl 35 castor oil, and process oil. Of these oily bases, perfluoropentane has temperature sensitivity and also has characteristics that it is volatilized at 29.5° C. Also, perfluorohexane, perfluorooctyl bromide and perfluorotributylamine have an external stimulation disruption property and have characteristics that cavitation is generated on the core of the carrier composition through external stimulation such as stimulation caused by irradiation with ultrasound, thereby causing core disruption.

When the carrier composition for nucleic acid delivery contains the oily base, the proportion of the oily base is not specifically limited as long as the effects of the invention are not adversely affected. The proportion of the oily base is from 0.1 to 50 parts by weight, preferably from 1 to 30 parts by weight, and more preferably from 5 to 20 parts by weight, per 100 parts by weight of the total amount of the components (A) to (C).

Furthermore, the carrier composition for nucleic acid delivery of the invention may contain a membrane-fusogenic lipid (helper lipid), if necessary. It becomes possible to further enhance efficiency of delivery of the nucleic acid into cells by containing such membrane-fusogenic lipid. Examples of the membrane-fusogenic lipid include dioleoylphosphatidylethanolamine, dioleoylphosphatidylcholine, transphosphatidylphosphatidylethanolamine, 1,2-bis(10,12-tricosadinoyl)-phosphoethanolamine, 1,2-dielaidoylphosphoethanolamine, 1,2-dihexadecylphosphoethanolamine, 1,2-dihexanoylphosphoethanolamine, 1,2-dilauroylphosphoethanolamine, 1,2-dilinoleoylphosphoethanolamine, 1,2-dimyristoylphosphoethanolamine, 1,2-dioleoylphosphoethanolamine, 1,2-dipalmitoleylphosphoethanolamine, 1,2-dipalmitoylphosphoethanolamine, 1,2-diphytanoylphosphoethanolamine, 1,2-distearoylphosphoethanolamine, 1-palmitoyl-2-oleoylphosphoethanolamine, 1-palmitoyl-2-(10,12-tricosadinoyl)phosphoethanolamine, 1,2-dioleoylphosphoethanolamine-N-caproylamine, 1,2-dipalmitoylphosphoethanolamine-N-caproylamine, 1,2-dioleoylphosphoethanolamine-N,N-dimethyl, 1,2-dipalmitoylphosphoethanolamine-N,N-dimethyl, 1,2-dipalmitoylphosphoethanolamine-N-dodecanoyl, 1,2-dioleoylphosphoethanolamine-N-dodecanoyl, 1,2-dioleoylphosphoethanolamine-N-dodecanylamine, 1,2-dipalmitoylphosphoethanolamine-N-dodecanylamine, 1,2-dioleoylphosphoethanolamine-N-glutaryl, 1,2-dipalmitoylphosphoethanolamine-N-glutaryl, 1,2-dioleoylphosphoethanolamine-N-lactose, 1,2-dioleoylphosphoethanolamine-N-[4(p-maleimidemethyl) cyclohexan e-carboxylate], dipalmitolylphosphoethanolamine-N-[4(p-maleimidemethyl)cyclohexan e-carboxylate], 1,2-dipalmitoylphosphoethanolamine-N-[4(p-maleimidephenyl)butyramide], 1,2-dioleoylphosphoethanolamine-N-[4 (p-maleimidephenyl) butyrate], 1,2-dioleoylphosphoethanolamine-N-methyl, dipalmitoylphosphoethanolamine-N-methyl, 1,2-dioleoylphosphoethanolamine-N-[3-(2-pyridyldithio)propionate], 1,2-dipalmitoylphosphoethanolamine-N-[3-(2-pyridyldithio)propionate], 1,2-dioleoylphosphoethanolamine-N-(succinyl), and 1,2-dipalmitoylphosphoethanolamine-N-(succinyl). Of these membrane-fusogenic lipids, dioleoylphosphatidylethanolamine is preferably used in the carrier composition for nucleic acid delivery of the invention.

When the carrier composition for nucleic acid delivery contains the membrane-fusogenic lipid, the proportion of the membrane-fusogenic lipid is not specifically limited as long as the effects of the invention are not adversely affected. The proportion of the membrane-fusogenic lipid is from 1 to 500 parts by weight, preferably from 10 to 250 parts by weight, and more preferably from 25 to 100 parts by weight, based on 100 parts by weight of the total amount of the components (A) to (C).

The carrier composition for nucleic acid delivery of the invention can contain various additives such as isotonizing agents, excipients, diluents, thickeners, stabilizers, buffers, and preservatives; and aqueous vehicles such as purified water, an aqueous saccharide solution, a buffer solution, a physiological saline, an aqueous polymer solution, and RNase free water, according to its form. The amounts of the additives and aqueous vehicles can be appropriately set according to the form of the carrier for nucleic acid delivery.

The form of carrier composition for nucleic acid delivery of the invention is not specifically limited as long as it can include the target nucleic acid to be delivered into cells, and the composition is preferably in the form of a liposome.

When the carrier composition for nucleic acid delivery of the invention is liposomal form, the components (A) to (C) and other lipids, which are optionally added, form a liposomal membrane. When the liposome is formed, it may be small unilamellar vesicles (SUV), large unilamellar vesicles (LUV), or multilamellar vesicles (MLV). Moreover, the particle diameter can be appropriately set according to the kind of cells to be delivered, for example, the particle diameter is 20 to 100 nm for SUV, 200 to 1,000 nm for LUV, and 400 to 3,500 nm for MLV. The particle diameter is determined using a dynamic light scattering method.

Production of the liposome and adjustment of its particle diameter are implemented according to methods which are common knowledge of one skilled in the art. More specifically, the liposome can be formed using an oil phase containing the components (A) to (C) and a water phase (aqueous vehicle) by a thin film method, a reverse-phase evaporation method, an ether infusion method, a surfactant method, and a heating method. Furthermore, the particle diameter can be adjusted by an extrusion method, a French press method, and a homogenization method.

The carrier composition for nucleic acid delivery of the invention is prepared by mixing the components (A) and (B) and, if necessary, other components, and appropriately forming the mixture into a preparation according to desired form.

Composition for Nucleic Acid Delivery

The composition for nucleic acid delivery of the invention contains the carrier composition for nucleic acid delivery and nucleic acid. Thus, the composition for nucleic acid delivery is used for introducing the nucleic acid contained in the composition into cells, which become the delivery target.

When the carrier composition for nucleic acid delivery is liposomal form, in the composition for nucleic acid delivery, the nucleic acid may exist in a state included in the aqueous phase of the liposome, or a state bound to the inside or outside of a liposomal membrane through an ionic or hydrophobic bond. In addition, if the carrier composition for nucleic acid delivery is not liposomal form, in the composition for nucleic acid delivery, it is only necessary to form a complex of the nucleic acid with components of the carrier composition for nucleic acid delivery through an ionic or hydrophobic bond.

The composition for nucleic acid delivery of the invention is prepared by mixing the carrier composition for nucleic acid delivery and nucleic acid, and forming the mixture into a desired form, or produced by mixing the nucleic acid and components of the carrier compositions for nucleic acid delivery in any order.

In the composition for nucleic acid delivery of the present invention, the mixing ratio of the nucleic acid and the carrier composition for nucleic acid delivery varies depending on the kind of nucleic acid, the carrier composition for nucleic acid delivery used, and the kind of cells of the delivery target. The proportion of nucleic acid is from $1.0 \times 10^{-5}$ to 1.0 parts by weight, preferably from $1.0 \times 10^{-4}$ to $1.0 \times 10^{-1}$ parts by weight, and more preferably from $1.0 \times 10^{-3}$ to $1.0 \times 10^{-2}$ parts, per 100 parts by weight of the total amount of the components (A) to (C) contained in the carrier composition for nucleic acid delivery.

Also, the total amount of the components (A) to (C) contained in the composition for nucleic acid delivery is from 10 to 90% by weight, preferably from 30 to 80% by weight, and more preferably from 40 to 60% by weight, based on the total amount of the composition.

The carrier composition for nucleic acid delivery of the invention can contain various additives such as isotonizing agents, excipients, diluents, thickeners, stabilizers, buffering agent, and preservatives; and aqueous vehicles such as purified water, an aqueous saccharide solution, a buffer, a physiological saline, according to its form. The amounts of the additives and aqueous vehicles can be appropriately set according to the form of the carrier for nucleic acid delivery.

In the invention, examples of the cells to which the nucleic acid is delivered include cultured cells, cells separated from living organisms (including established cell lines), and cells existing in living organisms such as human.

The form of the composition for nucleic acid delivery of the invention is not specifically limited as long as a proper amount of the composition for nucleic acid delivery is applied so as to be brought into contact with target cells into which the nucleic acid is introduced.

When the nucleic acid is delivered into cells existing in living organisms such as human, examples of the application include direct infusion into tissue; intravenous, subcutaneous, intramuscular, intraperitoneal, intraocular, digestive organic, and endodontic injections; inhalation administration to the nasal cavity, mouth cavity and lungs; oral administration; percutaneous administration through the skin; and mucosal administration through the oral mucous membrane, vaginal mucous membrane, ocular mucous membrane, rectal mucous membrane, and uterine mucous membrane. Alternatively, when the nucleic acid is delivered into cells separated from living organisms and cultured cells, a method of culturing cells in the presence of an appropriate amount of the composition for nucleic acid delivery added in advance of incubation is exemplified. In addition, when the nucleic acid is delivered into cells separated from living organisms or cultured cells, the nucleic acid can also be delivered into cells even in the presence of serum.

Amount of the composition for nucleic acid delivery of the invention applied to the delivery target cells is determined according to the kind of nucleic acid used, the kind of carrier composition for nucleic acid delivery used, and the kind of target cells. For example, when the delivery target are cells in human, therapeutically effective amount of the composition for nucleic acid delivery of the invention is administer to the patient of whom the therapeutic gain is expected by administering the nucleic acid.

EXAMPLES

The invention will now be described in detail based on Examples and the like, but the invention is not limited thereto. In the following Examples, distearoylphosphatidylcholine is abbreviated to "DSPC", dipalmitoylphosphatidylcholine is abbreviated to "DPPC", and dimyristoylphosphatidylcholine is abbreviated to "DMPC". In the following Test Examples 1 and 2, GL3-siRNA (siRNA to firefly luciferase; Dharmacon Co., Boulder, Colo., USA; sense: 5'-CUUACGCUGAGUACUUCGAdTdT, SEQ ID NO: 1, antisense: 5'-UCGAAGUACUCAGCGUAAGdTdT, SEQ ID NO: 2) was used as siRNA. In Test Example 3, Human MMP-9-siRNA (Samchully Pharm. Co., Ltd, Korea; Sense 5'-CCAACUAUGACCAGGAUAAdTdT-3', SEQ ID NO: 3, antisense: 5'-UUAUCCUGGUCAUAGUUGGdTdT-3', SEQ ID NO: 4) was used as siRNA.

Example 1

Preparation of DSPC-containing Carrier Composition for Nucleic Acid Delivery

DSPC, cholesterol and stearylamine were weighed in a molar ratio of 7:3:1 and then dissolved in chloroform using a recovery flask. The solution was dried under reduced pressure using a rotary evaporator to form a lipid thin-membrane. After DEPC-treated water (manufactured by Ambion Co.; Rnase free water) was added to the solution in such a manner that its DSPC concentration became 30 mg/mL, the particle diameter of the resulting solution was adjusted by passing through a membrane having a pore diameter of 100 nm using an extruder to prepare a carrier composition for nucleic acid delivery in a cationic liposomal form.

Example 2

Preparation of DPPC-containing Carrier Composition for Delivery of Nucleic Acid

In the same manner as in Example 1, except that DPPC was used in place of DSPC, a carrier composition for nucleic acid delivery in a cationic liposomal form was prepared.

Example 3

Preparation of DMPC-containing Carrier Composition for Delivery of Nucleic Acid

In the same manner as in Example 1, except that DMPC was used in place of DSPC, a carrier composition for nucleic acid delivery in a cationic liposomal form was prepared.

Example 4

Preparation of DSPC-containing Carrier Composition for Delivery of Nucleic Acid

A solution containing siRNA in a 2 μM concentration (siRNA solution) was prepared using a solution prepared by diluting 20× Tris-EDTA (TE) buffer (manufactured by Invitrogen Co.) 20 times with DEPC-treated water (manufactured by Ambion Co., Rnasefree water). Then, an equal amount of the carrier composition for nucleic acid delivery of Example 1 and the siRNA solution were mixed to form a lipoplex (complex), thus obtaining a composition for nucleic acid delivery.

Example 5

Preparation of DPPC-containing Carrier Composition for Delivery of Nucleic Acid

A solution containing siRNA in a 2 μM concentration (siRNA solution) was prepared using a solution prepared by diluting 20× Tris-EDTA (TE) buffer (manufactured by Invitrogen Co.) 20 times with DEPC-treated water (manufactured by Ambion Co., Rnasefree water). Then, an equal amount of the carrier composition for nucleic acid delivery of Example 2 and the siRNA solution were mixed to form a lipoplex (complex), thus obtaining a composition for nucleic acid delivery.

Example 6

Preparation of DMPC-containing Carrier Composition for Delivery of Nucleic acid

A solution containing siRNA in a 2 μM concentration (siRNA solution) was prepared using a solution prepared by diluting 20× Tris-EDTA (TE) buffer (manufactured by Invitrogen Co.) 20 times with DEPC-treated water (manufactured by Ambion Co., Rnasefree water). Then, an equal amount of the carrier composition for nucleic acid delivery of Example 3 and the siRNA solution were mixed to form a lipoplex (complex), thus obtaining a composition for nucleic acid delivery.

Test Example 1

Test for Evaluation of Safety for Cells

The evaluation was performed using a MTS assay. A CellTiter 96 Aqueous One Solution Cell Proliferation Assay manufactured by Promega Co. was used for the MTS assay. Specifically, A594 cells (ATCC, USA) were inoculated at $3.16 \times 10^4$ cells/well into 200 μl of Dulbecco's Modification of Eagle's Medium (DMEM) containing 10 vol % fetal bovine serum (FBS) in a 96-well plate, and incubated at 37° C. for 24 hours. After rinsing with Hank's Buffered Salt Solution (HBSS) 3 times, the medium was changed to DMEM without FBS, then 20 μl of each of the compositions for nucleic acid delivery of Examples 4 to 6 were added to each well and incubated at 37° C. under 5% $CO_2$ for 4 hours. Next, the culture supernatant in the wells was changed to DMEM with 10 vol % of FBS and incubated at 37° C. under 5% $CO_2$ for 20 hours again. 20 μl of a MTS (Methanethiosulfonate) reagent and 100 μl of a DMEM medium with 10 vol % FBS were added to each well, incubated for 2 hours, followed by determination of absorbance at 492 nm and further calculation of cell viability. The cell viability was calculated by setting the absorbance at 492 nm determined without adding the composition for nucleic acid delivery which was incubated under the above conditions as 100%.

The results are shown in FIG. 1. As shown in FIG. 1, it became apparent that all compositions for nucleic acid delivery of Examples 4 to 6 have low cytotoxicity and high safety. Particularly, it was confirmed that safety was significantly high in the compositions for nucleic acid delivery using DSPC or DPPC as the diacylphosphatidylcholine (Example 4 or 5).

Test Example 2

Test for Evaluation of siRNA Delivery Efficiency into Cells

Intracellular introduction of siRNA was evaluated by measuring fluorescence intensity of FITC-labeled siRNA using flow cytometry. In this test, a composition for nucleic acid delivery prepared with FITC pre-labeled siRNA was used. Specifically, A594 cells (ATCC, USA) were inoculated at $5 \times 10^5$ cells/well into 500 μl of DMEM with 10 vol % FBS in a 24-well plate, and incubated at 37° C. under 5% $CO_2$ for 24 hours. After rinsing three times with HBSS, the medium was changed to DMEM containing no FBS, and then 0.05 ml of each of the compositions for nucleic acid delivery of Examples 4 to 6 were added to each well and incubated at 37° C. under 5% $CO_2$ for 4 hours. Next, the culture supernatant in the wells was changed to DMEM with 10 vol % of FBS and incubated at 37° C. under 5% $CO_2$ for 20 hours again. Each well was rinsed with HBSS once and 0.2 mL of CellScrubBuffer (Gene Therapy Systems, Inc.) was added, followed by incubation at 37° C. under 5% $CO_2$ for 15 minutes. Again, the wells were rinsed with HBSS 2 times and cells attached on the well bottom were detached using trypsin and collected by centrifugation, and then the resulting cells were suspended in HBSS. The suspension was filtered through a membrane having a pore diameter of 41 μm. Fluorescence intensity of cells was measured using flow cytometry at 2 hours and 24 hours after the addition of the compositions for nucleic acid delivery. As a control, fluorescence intensity of a control composition for nucleic acid delivery obtained by mixing a solution of Lipofectamine 2000™ (Invitrogen) often used as a commercially-available gene vector diluted with OptiMEM media to 0.1 mg/mL and siRNA solution diluted with TE buffer at a concentration of 2 μM in a volume ratio of 1:1 was also measured in the same manner as described above.

Figure 2:
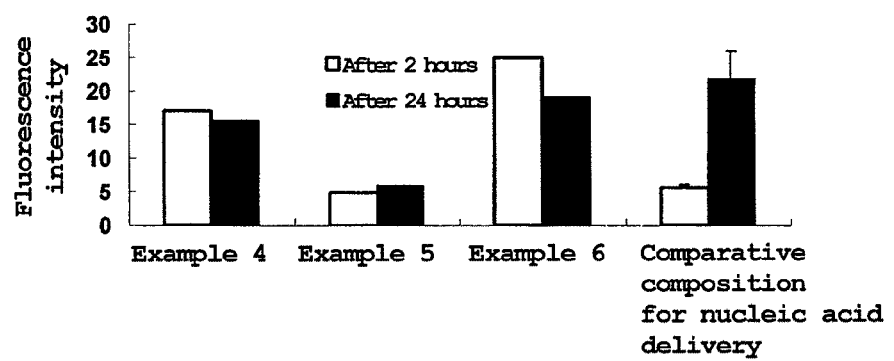
FIG. 2 shows the results of the evaluation of siRNA introduction into cells mediated by each composition for nucleic acid delivery in Test Example 2. The ordinate in FIG. 2 indicates the average fluorescence intensity per one cell.

The results are shown in FIG. 2. From these results, it was confirmed that siRNA is incorporated into cells in any case of compositions for nucleic acid delivery of Examples 4 to 6. Particularly, in the compositions for nucleic acid delivery using DSPC or DMPC as the diacylphosphatidylcholine (Examples 4 and 6), it became apparent that introduction of siRNA 2 hours after addition was significantly high as compared with Lipofectamine 2000 often used as a commercially-available gene vector and that the compositions have favorable characteristics in excellent fast-acting.

Figure 3:
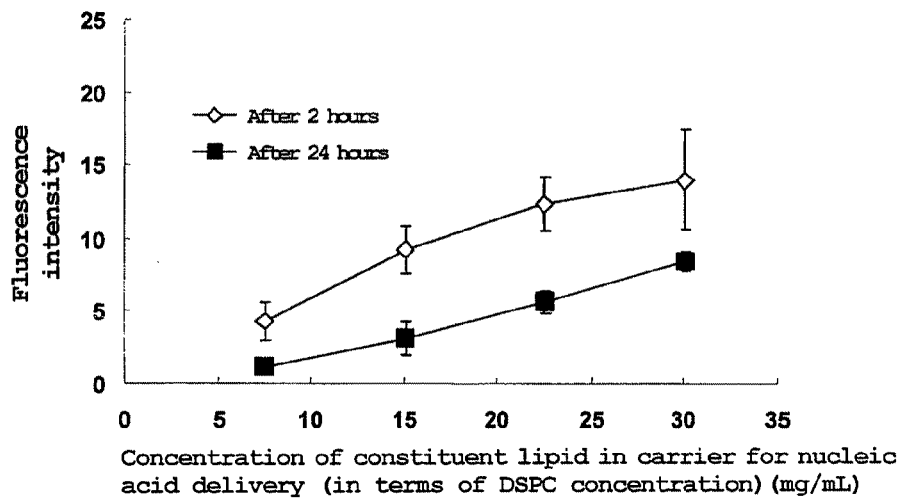
FIG. 3 shows the results of the evaluation of siRNA introduction into cells when the concentration of the constituent lipids (DSPC, cholesterol and stearylamine) of the carrier for nucleic acid delivery is changed in a composition for nucleic acid delivery in Test Example 2.

Furthermore, a carrier for nucleic acid delivery having a DSPC concentration of 7.5 to 30 mg/mL was produced according to the same manner as in Example 1, using DSPC, cholesterol, and stearylamine (DSPC:cholesterol:stearylamine=7:3:1 in a molar ratio, hereinafter, collectively referred to as a "constituent lipid of the carrier for nucleic acid delivery"). A lipoplex (complex) was formed by mixing an equal amount of this carrier for nucleic acid delivery and TE buffer containing 200 nM siRNA, and the composition for nucleic acid delivery were prepared. Using the composition for nucleic acid delivery prepared in this manner, introduction of siRNA into cells was evaluated in the same manner as described above. The results are shown in FIG. 3. From these results, when the concentration of the constituent lipid of the carrier for nucleic acid delivery was changed, the amount of nucleic acid introduced into cells mediated by the composition for nucleic acid delivery was changed accordingly. Also, it was found that the constituent lipid of the carrier for nucleic acid delivery shows a low value in the introduced siRNA amount at 24 hours after addition as compared with 2 hours after addition at any concentration, and that disappearance of siRNA started at 24 hours after addition. Therefore, the results also revealed that it is possible to deliver siRNA into cells within a short time of 2 hours after addition by using the combination of DSPC, cholesterol, and stearylamine as the carrier for nucleic acid delivery, and that the compositions have favorable characteristics in excellent fast-acting.

Test Example 3

Test for Evaluation of Inhibition of Interferon Induction

A594 cells (ATCC, USA) were inoculated at $5 \times 10^5$ cells/well into 500 µl of DMEM with 10 vol % FBS in a 24-well plate, and incubated at 37° C. under 5% $CO_2$ for 24 hours. After rinsing three times with HBSS, a 450 µl of DMEM medium containing no FBS was added into each well, moreover, 50 µl of the composition for nucleic acid delivery of Example 4 was added into each well and incubated at 37° C. under 5% $CO_2$ for 4 hours. Next, the culture supernatant in the wells was changed to DMEM with 10 vol % of FBS and incubated at 37° C. under 5% $CO_2$ for 20 hours again. After rinsing three times with HESS, cells attached on the well bottom were detached using trypsin and collected by centrifugation. RNA was extracted from the resulting cells using Rneasy Plus Mini (Qiagen), and then cDNA was obtained by transcription using QutantiTect Reverse Transcription (Qiagen). Using the resulting cDNA, QutantiTectPrimer Assay (Qiagen), and iCycler iQ (Bio-RAD), mRNA of IFIT-1, which is an interferon-inducing gene, was quantified with real-time PCR. As a control, mRNA of IFIT-1 was quantified in a control composition for nucleic acid delivery obtained by mixing a solution of Lipofectamine 2000™ (Invitrogen) often used as a commercially-available gene vector diluted with OptiMEM media to 0.1 mg/mL and the siRNA solution diluted with TE buffer at concentration of 2 µM in a volume ratio of 1:1 in the same manner as described above. As a housekeeping gene to correct the quantification, 18rRNA was used. Also, as a blank, mRNA of IFIT-1 was quantified with the above conditions without the addition of the composition for nucleic acid delivery.

Figure 4:
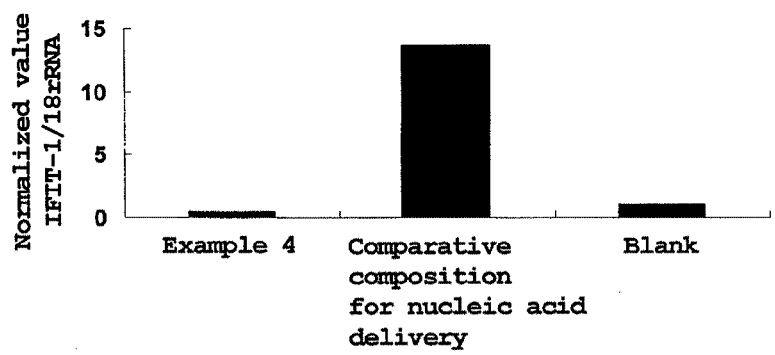
FIG. 4 shows the evaluation results of the inhibition of interferon induction by a siRNA-containing composition for nucleic acid delivery in Test Example 3.

The results are shown in FIG. 4. The composition for nucleic acid delivery of Example 4 using DSPC indicated significantly low induction of interferon as compared with the control composition for nucleic acid delivery using Lipofect™ amine 2000. The results revealed that it is possible to inhibit induction of interferon, which is an adverse effect of siRNA, using the composition for nucleic acid delivery of the present invention.

The invention claimed is:

1. A composition for delivery of siRNA comprising an siRNA, and a carrier composition for delivery of siRNA, consisting essentially of (A) at least one member selected from the group consisting of dimyristoylphosphatidycholine and distearoylphosphatidylcholine , (B) cholesterol , and (C) an aliphatic primary amine, wherein the molar ratio of component (A): component (B): component (C) is 6-9:1-4:1, wherein the total amount of components (A) to (C) contained in the composition for delivery of siRNA is from 30 to 90% by weight, based on the total amount of the composition.

2. The composition for delivery of siRNA according to claim 1, wherein the component (C) is an alkylamine having 10 to 20 carbon atoms.

3. The composition for delivery of siRNA according to claim 1,
wherein the component (A) is at least one member selected from the group consisting of dimyristoylphosphatidylcholine, and distearoylphosphatidylcholine;
the component (B) is cholesterol; and
the component (C) is stearylamine.

4. The composition for delivery of siRNA according to claim 1, wherein the carrier composition for delivery of siRNA is a liposome preparation in which a liposomal membrane is formed of the components (A) to (C).

5. The composition for delivery of siRNA according to claim 1, wherein the composition is a liposomal preparation.

6. A method for introducing a siRNA, which comprises the step of introducing the siRNA into cells by bringing the composition for of siRNA delivery of claim 1 into contact with the cells.

7. A method for introducing a siRNA according to claim 6, wherein the cells are cultured cells, cells separated from living organisms, or cells existing in living organisms.

* * * * *

SEQUENCE LISTING

```
<160> NUMBER OF SEQ ID NOS: 4

<210> SEQ ID NO 1
<211> LENGTH: 21
<212> TYPE: DNA
<213> ORGANISM: artificial
<220> FEATURE:
<223> OTHER INFORMATION: GL3-siRNA

<400> SEQUENCE: 1
cuuacgcuga guacuucgat t                                              21

<210> SEQ ID NO 2
<211> LENGTH: 21
<212> TYPE: DNA
<213> ORGANISM: artificial
<220> FEATURE:
<223> OTHER INFORMATION: GL3-siRNA

<400> SEQUENCE: 2
ucgaaguacu cagcguaagt t                                              21

<210> SEQ ID NO 3
<211> LENGTH: 21
<212> TYPE: DNA
<213> ORGANISM: artificial
<220> FEATURE:
<223> OTHER INFORMATION: MMP-9-siRNA

<400> SEQUENCE: 3
ccaacuauga ccaggauaat t                                              21

<210> SEQ ID NO 4
<211> LENGTH: 21
<212> TYPE: DNA
<213> ORGANISM: artificial
<220> FEATURE:
```

```
<223> OTHER INFORMATION: MMP-9-siRNA

<400> SEQUENCE: 4
uuauccuggu cauaguuggt t                                                        21
```